United States Patent [19]
Ventura et al.

[11] Patent Number: 5,675,417
[45] Date of Patent: *Oct. 7, 1997

[54] INFINITELY ADJUSTABLE AUTOMOBILE BODY REPAIR LIGHT PANEL SUPPORT

[75] Inventors: George Ventura, Bonner Springs, Kans.; James D. Jenkins, Lee's Summit; Winford D. McClain, Kansas City, both of Mo.

[73] Assignee: It's Dents or Us, Inc., Overland Park, Kans.

[*] Notice: The term of this patent shall not extend beyond the expiration date of Pat. No. 5,436,726.

[21] Appl. No.: 432,797

[22] Filed: May 2, 1995

Related U.S. Application Data

[63] Continuation-in-part of Ser. No. 247,640, May 23, 1994, Pat. No. 5,436,726.

[51] Int. Cl.⁶ .................................................. G01N 21/00
[52] U.S. Cl. .................................................. 356/371; 356/237
[58] Field of Search .................................... 356/237, 371, 356/376; 250/237 G

[56] References Cited

U.S. PATENT DOCUMENTS

| | | |
|---|---|---|
| 4,448,527 | 5/1984 | Milana. |
| 4,585,350 | 4/1986 | Pryor ............................... 356/376 |
| 4,629,319 | 12/1986 | Clarke et al.. |
| 4,792,232 | 12/1988 | Jobe et al.. |
| 5,090,804 | 2/1992 | Wong et al.. |
| 5,168,322 | 12/1992 | Clarke et al.. |
| 5,206,700 | 4/1993 | Reynolds et al.. |
| 5,225,890 | 7/1993 | Lee et al.. |
| 5,237,404 | 8/1993 | Tanaka et al. ...................... 356/376 |
| 5,436,726 | 7/1995 | Ventiera et al. .................... 356/237 |

FOREIGN PATENT DOCUMENTS

| | | |
|---|---|---|
| 269006 | 11/1988 | Japan. |
| 264448 | 10/1993 | Japan. |

OTHER PUBLICATIONS

Hugh W. Lippincott and Henry Stark; Optical–Digital Detection of Dents and Scratches on Specular Metal Surfaces; Aug. 15, 1982; *Applied Optics*, vol. 21, No. 16, pp. 2875–2881.

*Primary Examiner*—Richard A. Rosenberger
*Attorney, Agent, or Firm*—Litman, McMahon and Brown, L.L.C.

[57] ABSTRACT

A light panel for highlighting flaws and imperfections in the surface of an automobile body or the like includes a pair of lenses with one lens positioned on each side of a light source. The lens on one side of the panel is yellow with a painted black stripe thereon with the black stripe irregularly "bleeding" into the yellow to create diverse shadow lines. The lens on the opposite side of the panel is white with a similar black stripes. Each black stripe includes a narrow centerline of white or black, respectively which serves as a reference. A fluorescent lamp is positioned between the lenses to project a shadow line light pattern onto the surface to be inspected for dents or imperfections. The white and black shadow line pattern is more effective at highlighting flaws in darker colored surfaces while the yellow and black shadow line pattern is more effective at highlighting flaws in lighter colored surfaces. An infinitely adjustable light panel support frame allows the light panel to be positioned at any desired height and oriented at any desired orientation to effectively illuminate and highlight any desired portion of an automobile body.

8 Claims, 3 Drawing Sheets

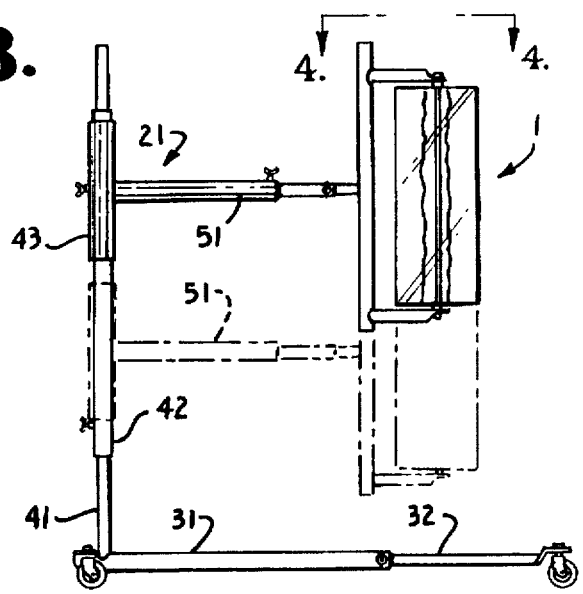
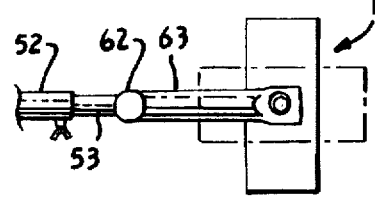
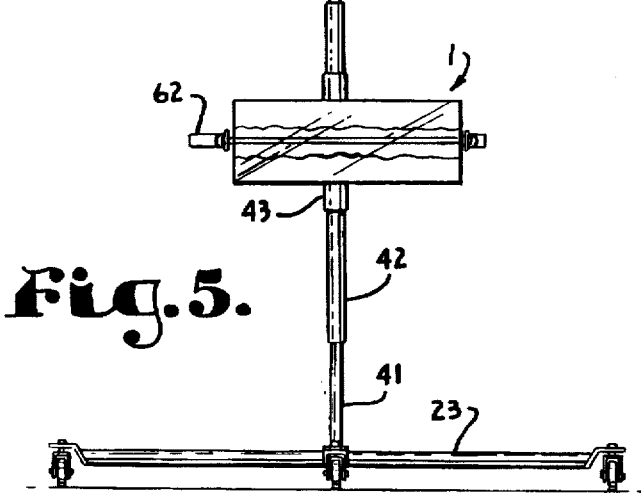
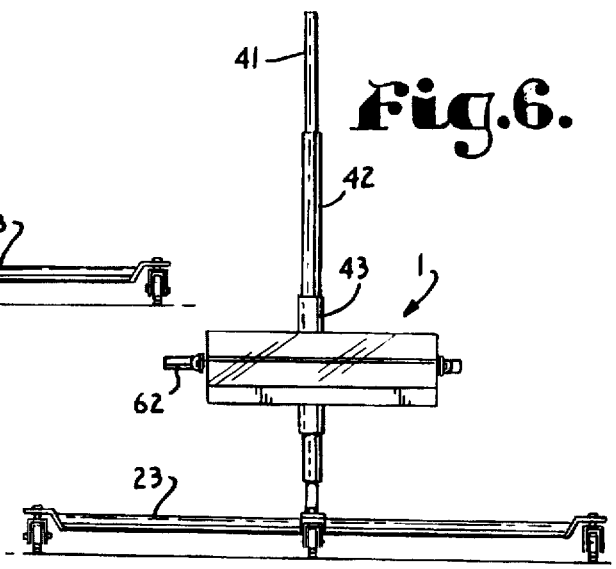

INFINITELY ADJUSTABLE AUTOMOBILE BODY REPAIR LIGHT PANEL SUPPORT

CROSS REFERENCE TO RELATED APPLICATIONS

This application is a continuation-in-part of application Ser. No. 08/247,640, entitled FLAW HIGHLIGHTING LIGHT PANEL AND BOOTH FOR AUTOMOBILE BODY REPAIR, filed May 23, 1994 U.S. Pat. No. 5,436,726.

BACKGROUND OF THE INVENTION

I. Field of the Invention

The present invention relates to an infinitely adjustable support for an automobile body inspection light panel, and more particularly to such a support which can hold such a light panel at any desired height and orientation for inspecting and facilitating automobile body repairs.

II. Description of the Related Art

It is often difficult to detect small dents and other imperfections in the surface of an automobile body by unaided eyesight. This is particularly true of new or newly painted automobiles viewed under artificial light, such as in automobile assembly plants or repair and paint shops. In such assembly plants and repair shops, it is important that even the smallest dent or imperfection be detected to provide for satisfied customers and dealers and to avoid adversely affecting the reputation of the plant or shop.

Several previous efforts have been made to produce inspection systems for metal surfaces which are designed to detect surface dents and scratches. Hugh Lippincott and Henry Stark, in an article entitled "Optical-digital detection of dents and scratches on specular metal surfaces" in *Applied Optics*, Aug. 15, 1982, describe a system in which a regular grid pattern is reflected off of a metal surface to be inspected, with the reflected image photographed by a video camera. The photographs are then digitally analyzed and compared against samples from a calibration sample from an unflawed surface with any large deviations indicating the presence of one or more dents. For scratch detection, the authors describe a gray level threshold analysis to detect background to scratch brightness contrasts. The system described in the *Applied Optics* article was designed for and appears to be most suitable for implementation in an environment in which relatively small manufactured appliances must be inspected automatically, with badly scratched or dented samples simply discarded or recycled.

A series of U.S. Patents describe a retroreflective surface inspection system and method, including U.S. Pat. No. 4,629,319 to Clarke et al., U.S. Pat. No. 5,168,322 to Clarke et al., and U.S. Pat. No. 5,206,700 to Reynolds et al., all of which are assigned to Diffracto, Ltd. of Windsor, Canada. In these patents, light from a slit or point source is swept across a surface to be inspected via a scanning mirror or the like. The light reflects off of the inspected surface, off of a retroreflective surface and back off of the inspected surface and then to a camera lens or the eye of an observer. The retroreflected image received by the camera or eye magnifies any dents or imperfections in the surface being inspected. These systems employ sophisticated robotic inspectors and require complex synchronization of the swept beam and the analyzing equipment. For use in an automobile assembly plant or the like, the patents illustrate an inspection system with multiple independent light emitters, reflectors and analyzers. In addition, these patents describe an inspection process in which inspected panels must first be covered with a thin coating of oil to enhance their reflective properties. This is an expensive and time consuming process. Finally, in the Diffracto systems, as well as the Lippincott and Stark article, a sophisticated digital analysis must be performed and interpreted, which effectively limits the possibility of immediate correction of detected dents or other defects.

It is clear then, that an effective apparatus and method is needed for highlighting flaws and imperfections in automobile bodies. Such an apparatus and method should be inexpensive and reliable, should allow flaws and imperfections to be detected quickly and efficiently by an ordinary observer, should be effective at highlighting flaws in automobiles of a wide variety of colors and should allow detected dents and blemishes to be repaired immediately during the inspection process. Such a highlighting apparatus should be capable of convenient transport to an automobile to be inspected, and should be held at any desired height and angle for facilitating such inspections.

SUMMARY OF THE INVENTION

The present invention is directed to an infinitely adjustable support for a portable automobile body inspection light panel for holding the light panel at any desired height and orientation relative to an automobile to facilitate inspection of the automobile body surface for flaws or imperfections.

Such portable light panels include a fluorescent backlight fixture enclosed between two diverse transparent lenses. The lens on one side is colored translucent white and has an opaque black stripe painted or otherwise applied thereon, with a narrow centerline left white. The lens on the opposite side is colored translucent yellow with a similar opaque black stripe painted thereon, again with a narrow centerline left as yellow. Depending upon the color of the automobile being inspected, one or the other side of the light box is turned toward the automobile to project a light pattern onto the automobile body surface.

The projected light pattern highlights the visibility of any flaws or imperfections in the body surface by magnifying an observer's perception of relative depth differences between the flaw and the unflawed body surface. The white lens side is used for automobiles with darker shades of color, such as black, navy blue, maroon, etc. while the yellow lens side is more effective at highlighting and enhancing imperfections in lighter colored automobiles, such as white, light gray, light blue, etc.

The black stripes are painted or otherwise applied to the yellow and white lenses in a fashion such that the black color irregularly "bleeds" into the yellow or white. This technique forms shadow areas between translucent yellow and opaque black, which shadow areas are projected onto the automobile by the backlights. The thus created shadow lines form light patterns on the automobile body which highlight any dents or imperfections in the automobile body surface by making the dents appear darker than the surrounding smooth surface, which appears to shine by contrast. The narrow centerlines are positioned to serve as a reference in aligning the light panel, i.e. the centerline projects a narrow strip of light within a dark band so that the dark band can be centered on a dent to be repaired.

The inventive light panel support includes a frame with a base including a first elongate base support tube to which are attached first and second free castering wheels, one at either end of the first support tube. Attached approximately in the middle of the first elongate support tube and extending orthogonally outward therefrom is a second base support tube with a smaller diameter telescoping extension tube received thereby. A third free castering wheel is attached at the end of the telescoping extension tube. The combination of the second base support tube and the telescoping extension tube is thus adjustable in length. Proximate the intersection of the first and second base support tubes, a first substantially vertically oriented tube is attached to the base and extends upward therefrom. A second, somewhat larger diameter vertically oriented tube is telescopically attached over the first vertically oriented tube and a third, still larger diameter vertically oriented tube is, in turn, telescopically attached over the second tube. Attached to the third vertical tube and extending substantially horizontally outward therefrom is a first horizontal support tube. A second, smaller diameter horizontal tube is telescopically received inside the first horizontal support tube and a third, still smaller diameter horizontal tube is telescopically received within the second horizontal support tube. The third horizontal tube is attached to one side of an elongate light panel support rod and a pair of opposed panel support arms are attached to the opposite side of the panel support rod. The support arms are spaced from each other at a distance which accommodates the light panel therebetween, with the light panel being rotatably attached thereto.

With the light panel thus supported, light from either side of the reversible panel can be selectively directed toward an automobile body at any desired height and with any desired orientation such that dents and imperfections can be reliably detected on any portion of the automobile body.

OBJECTS AND ADVANTAGES OF THE INVENTION

The objects and advantages of the present invention include: providing a portable light panel which highlights flaws and imperfections in an automobile body surface; providing such a light panel which includes a specially colored lens or lenses which, when backlighted, project light patterns and shadow lines onto the automobile body which patterns highlight any imperfections in the surface; providing such a light panel which has a translucent white and opaque black striped lens on one side for highlighting surface flaws in darker colors and a translucent yellow and opaque black striped lens on the opposite side for highlighting surface flaws in lighter colors; providing such a portable light panel in which each opaque black stripe includes a narrow centerline of translucent white or yellow to serve as a centerline reference; providing a light panel support which is easily transportable; providing such a light panel support which is infinitely adjustable such that the light panel can be placed at virtually any desired height and with any desired orientation with respect to an automobile body to be inspected; and providing such a light panel and light panel support which is reliable, inexpensive and relatively simple to manufacture and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is a reduced side elevational view of the light panel and light panel support with the light panel shown in a raised position in solid lines and in a lowered position in phantom lines.

FIG. 4 is a reduced, fragmentary top plan view of a portion of the support and the light panel, taken along line 4—4 of FIG. 3 and showing the light panel oriented orthogonal to the longitudinal axis of the horizontal support tube in solid lines and rotated to a position in alignment with the longitudinal axis of the horizontal tube in phantom lines.

FIG. 5 is a reduced, front elevational view of the light panel and light panel support with the light panel oriented to direct light approximately horizontally toward a side panel, for example, of an automobile body.

FIG. 6 is a reduced, front elevational view of the light panel and light panel support with the light panel oriented at an upward angle to direct light toward an underside, for example, of an automobile body.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
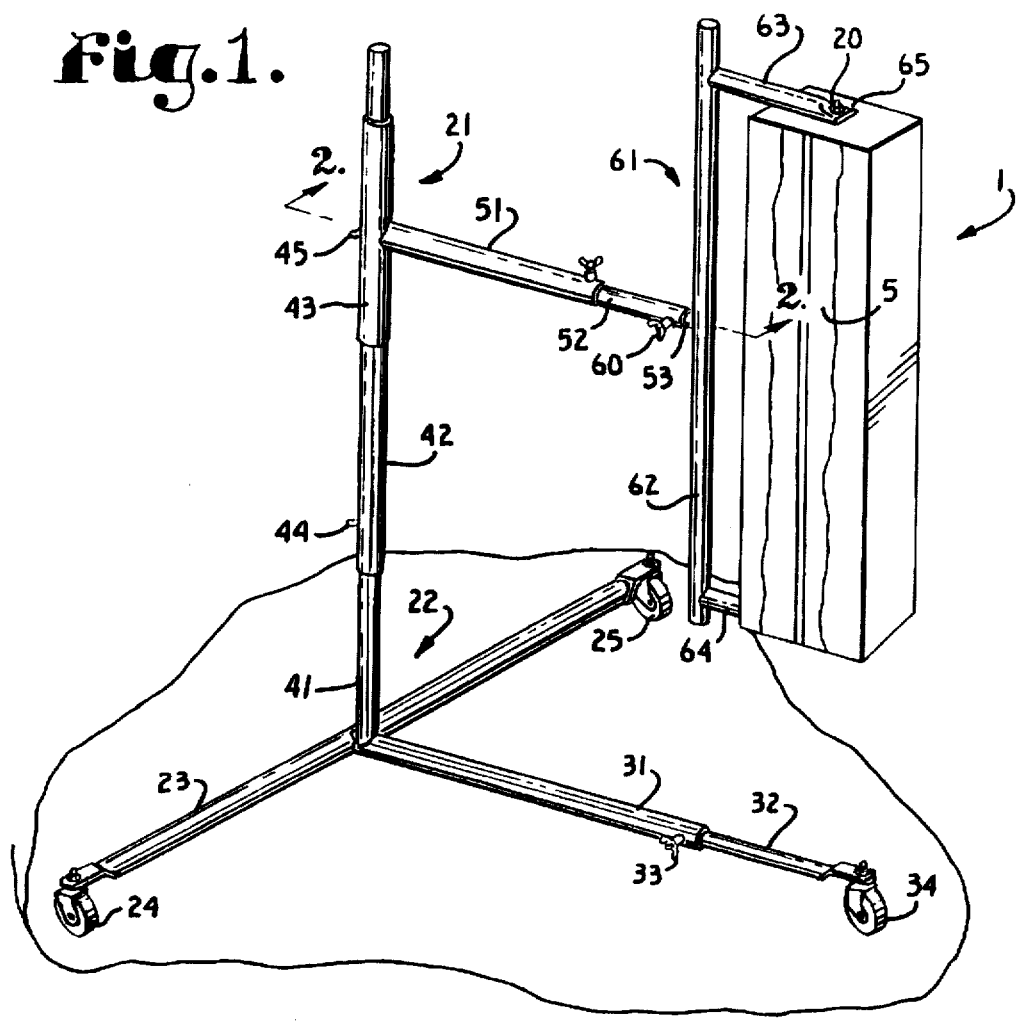
FIG. 1 is a perspective view of a portable light panel being supported by a light panel support in accordance with the present invention.
Figure 8:
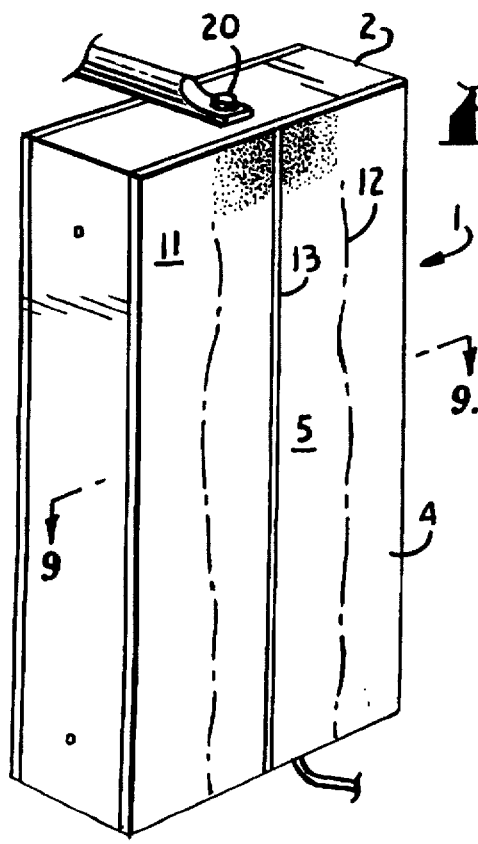
FIG. 8 is a greatly enlarged, fragmentary perspective view of the invention of FIG. 1, illustrating the automobile body inspection light panel in greater detail.
Figure 9:
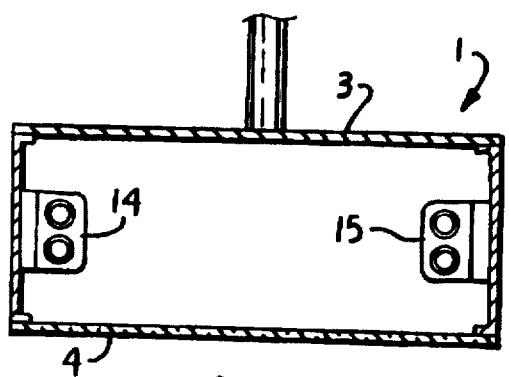
FIG. 9 is a cross-sectional view of the light panel, taken along line 9—9 of FIG. 8, and illustrating the internal construction thereof and the orientation of opposite facing, differently colored lenses.

Referring to the drawings in greater detail, and in particular to FIGS. 1, 8 and 9, a single, portable light panel 1 is illustrated. The panel 1 includes an enclosed box 2 and opposite facing lenses 3 and 4. Each lens 3 and 4 is of a translucent, light color with a centered, opaque, dark colored stripe 5, which leaves outside bands 11 of the original light color. The light colored bands 11 on the lens 3 are preferably translucent yellow while the bands 11 on the lens 4 are preferably translucent white. The yellow lens 3 is more effective for inspection of lighter colored automobiles, such as white, light gray, silver, etc. while the white lens 4 is more effective for darker colored automobiles, such as dark gray, black, brown, etc. The dark stripes 5 tend to bleed into the light bands 11, creating a wavy and indistinct shadow line 12 therebetween. A narrow centerline 13 of the original light color of each lens is left for a reference in centering a dent to be repaired in the dark stripe. A pair of backlighting fluorescent lamps 14 and 15 are positioned on either side of the enclosed panel 1. A pair of mounting bolts 21 extend outward from opposite threaded bores (not shown) in the ends of the panel 1 for attachment to a support frame assembly 21.

The support frame assembly 21 includes a base assembly 22 including a first elongate base support tube 23 to which are attached first and second free castering wheels 24 and 25, one at either end of the first base support tube 23. The base assembly 22 also includes a second base support tube 31 attached approximately in the middle of the first elongate support tube and extending orthogonally outward therefrom. A smaller diameter telescoping extension base support tube 32 is received within the second base support tube and is telescopically adjustable relative thereto. A wing bolt 33 extends through a threaded bore (not shown) in the second base support tube 31 to selectively contact the extension tube 32 to secure it in a selected extension position. A third free castering wheel 34 is attached at the end of the telescoping extension tube 32, with the wheels 24, 25 and 34 providing support and mobility for the panel support frame 21.

Proximate the intersection of the first and second support tubes 23 and 31, respectively, a first substantially vertically oriented tube 41 is attached to the second support tube 32 and extends upward therefrom. A second, somewhat larger diameter vertically oriented tube 42 is telescopically attached over the vertically oriented tube 41 and a third, still larger diameter vertically oriented tube 43 is, in turn, telescopically attached over the second robe 42. A wing bolt 44 extends through a threaded bore (not shown) in the second vertical tube 42 to selectively contact the first tube 41 to secure it in a selected extension position and a wing bolt 45 extends through a threaded bore 46 in the third vertical tube 43 to selectively contact the second tube 42 to secure the third tube 43 in a selected extension position.

Figure 2:
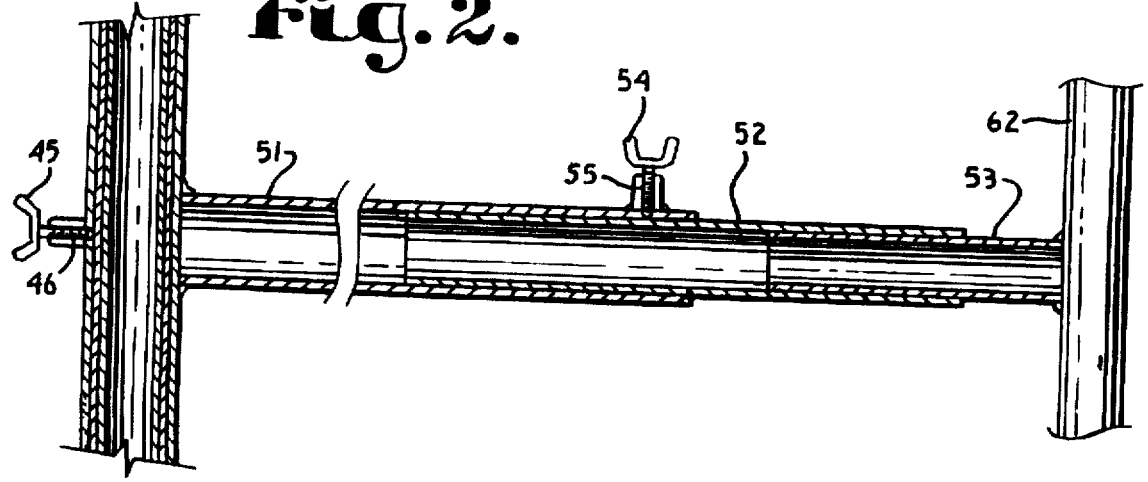
FIG. 2 is a greatly enlarged, fragmentary cross-sectional view taken along the line 2—2 of FIG. 1, and illustrating a telescoping horizontal support tube.

Referring to FIGS. 1 and 2, attached to the third tube 43 and extending substantially horizontally outward therefrom is a first horizontal support tube 51. A second, smaller diameter horizontal support tube 52 is telescopically received inside the first panel support robe and a third horizontal support tube 53 is telescopically received within the second support tube 52. The third support tube 53 is both extendable and rotatable relative to the second support tube 52. A wing bolt 54 extends through a threaded bore 55 in the first horizontal support tube 51 to selectively contact the second support tube 52 to secure it in a selected extension position and a wing bolt 60 extends through a threaded bore (not shown) in the second horizontal support tube 52 to selectively contact the third tube 53 to secure the third tube 53 in a selected extension and rotation position.

A panel support assembly 61 including an elongate light panel support rod 62 is attached, via welding or the like, at one side of the rod 62 to the third horizontal support tube 53. A pair of opposed panel support arms 63 and 64 are attached to the opposite side of the panel support rod 62. The support arms 63 and 64 are spaced from each other at a distance which accommodates the light panel 1 therebetween. Each of the arms 63 and 64 is tapered at the end with an aperture 65 extending through each tapered end to accommodate the bolt 20 extending therethrough into a threaded bore (not shown) in either end of the panel 1. The light panel 1 is thus rotatably attached between the panel support arms 63 and 64.

FIGS. 3–6 are illustrative of the wide variety of positions and orientations for the light panel 1 which can be achieved by the support 21. The light panel support frame 21 is infinitely adjustable, allowing the light panel 1 to be readily moved from high to low positions, as shown in solid and phantom lines, respectively, in FIG. 3. Similarly, the light panel 1 can be telescoped toward and away from the vertical support rod 41 and can be rotatably adjusted relative to the support arms 63 and 64, as shown in FIGS. 4, 5 and 6. Finally, the panel support assembly 61 is rotatably adjustable relative to the horizontal support tube 52, as illustrated by the different orientations in FIGS. 3 and 5, respectively.

Figure 7:
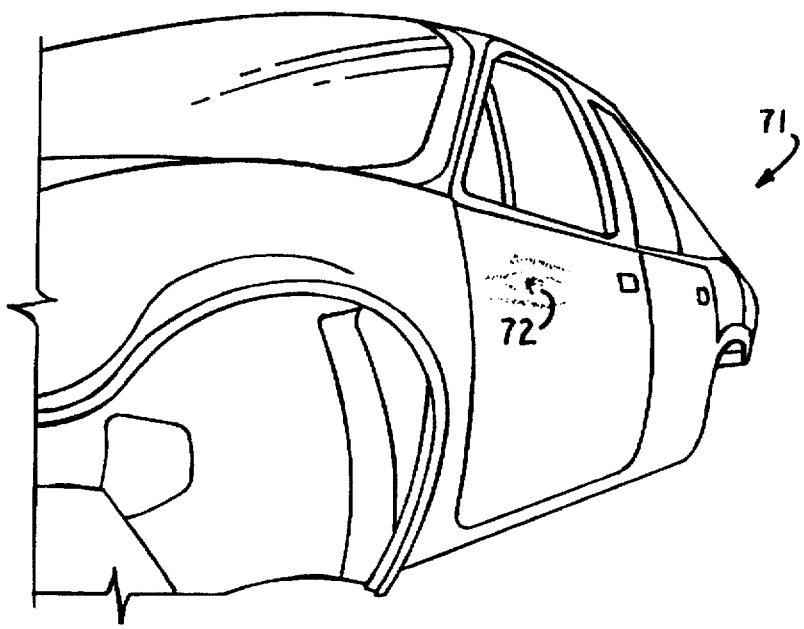
FIG. 7 is a fragmentary, perspective view of an automobile body with a dent being highlighted with light from the inventive light panel supported by the light panel support.

With the light panel 1 thus infinitely adjustably supported by the support frame 21, light from either lens 3 or 4 of the reversible panel 1 can be selectively directed toward an automobile body, such as the body 71 in FIG. 7, at any desired height and with any desired orientation. Thus, dents and imperfections such as the dent 72 in the automobile body 71, can be reliably detected on any portion of the automobile body.

The portable light panel 1 combined with the support frame 21, is ideal for use in automobile body shops, for example, where the auto bodies to be repaired are stationary. A workman who is to straighten a portion of an automobile body, such as a fender, for example, will position the panel 1 such that it shines an optical shadow line pattern onto the fender, with the projected centerline 13 centered in the dent to be repaired. The workman observes the light pattern reflected by the fender continuously while he straightens the dent. With the inventive light panel support, the workman can constantly highlight the fender as he straightens the dent, thus making him immediately aware of when the dent is straightened, or when further straightening is needed.

It is to be understood that while certain forms of the present invention have been illustrated and described herein, it is not to be limited to the specific forms or arrangement of parts described and shown.

What is claimed and desired to be secured by Letters Patent is as follows:

1. A combination light panel for inspecting a surface for imperfections and an infinitely adjustable support frame for said light panel:

a. said panel comprising
    i. a framework with first and second sides;
    ii. a light source supported by and positioned on said framework between said first and second sides; and
    iii. a first lens at least partially covering said first side of said framework and said light source, said first lens including a first pattern with alternating light colored bands and opaque dark colored stripes, said first lens projecting light from said light source in said first pattern onto said surface to be inspected, when said first lens is facing said surface, to highlight flaws and imperfections in said surface; and
    iv. a second lens at least partially covering said second side of said framework and said light source, said second lens including a second pattern with alternating light colored bands and opaque dark colored stripes, said light colored bands in said second pattern being of a different color than those in said first pattern, said second lens also projecting light from said light source in said second pattern onto the surface to be inspected, when said second lens is facing said surface, to highlight flaws and imperfections in said surface; and
  b. said frame comprising:
    i. a base assembly;
    ii. a substantially vertically oriented telescoping support assembly;
    iii. a substantially horizontally oriented telescoping support assembly; and
    iv. a panel support assembly rotatably attached to said horizontally oriented support assembly, said panel support assembly comprising a pair of support arms spaced and positioned to support said panel therebetween, said panel being rotatable relative to said support arms such that either side of said panel can be selectively directed toward the surface to be inspected.

2. A combination light panel and support frame as in claim 1, wherein:
   a. each of said dark stripes in said first and second patterns is applied to the respective lens such that the dark color bleeds into the light colored bands to form shadow lines in said light patterns.

3. A combination light panel and support frame as in claim 1, wherein:
   a. each of said opaque dark colored stripes includes a narrow centerline of said translucent light color.

4. A combination light panel and support frame as in claim 1, wherein:
   a. said first pattern includes alternating yellow and black stripes.

5. A combination light panel and support frame as in claim 4, wherein:
   a. said first pattern of alternating yellow and black stripes is effective for highlighting defects in lighter colored surfaces.

6. A combination light panel and support frame as in claim 4, wherein:
   a. said second pattern includes alternating white and black stripes.

7. A combination light panel and support frame as in claim 4, wherein:
   a. said second pattern of alternating white and black stripes is effective for highlighting defects in darker colored automobile bodies.

8. A combination light panel and support frame as in claim 1, wherein:
   a. said lighting means comprises a fluorescent light fixture.

* * * * *